United States Patent [19]

Mattson et al.

[11] Patent Number: 5,780,470
[45] Date of Patent: Jul. 14, 1998

[54] MELATONERGIC INDANYL PIPERAZINES

[75] Inventors: Ronald J. Mattson, Meriden; John D. Catt, Southington, both of Conn.

[73] Assignee: Bristol-Myers Squibb Company, Princeton, N.J.

[21] Appl. No.: 634,329

[22] Filed: Apr. 18, 1996

Related U.S. Application Data

[63] Continuation-in-part of Ser. No. 458,925, Jun. 2, 1995, abandoned.

[51] Int. Cl.$^6$ ............... A01N 43/60; A61K 31/495
[52] U.S. Cl. ............... 514/247; 514/252; 514/255; 544/336; 544/404
[58] Field of Search ............... 514/218, 247, 514/252, 255; 540/575; 544/336, 404

[56] References Cited

U.S. PATENT DOCUMENTS 4,963,680  10/1990  Manoury et al. ............... 544/395

FOREIGN PATENT DOCUMENTS 2 687 401   8/1993   France.

OTHER PUBLICATIONS

Dubocovich, et al., "Antidepressant–like activity of the melatonin receptror antagonist, luzindole (N–0774), in the mouse behavioral despair test," *European Journal of Pharmacology.*, 182: 313–325 (1990).

*Primary Examiner*—Jeffrey C. Mullis
*Attorney, Agent, or Firm*—Aldo A. Algieri

[57] ABSTRACT

Certain indanyl piperazines are useful as melatonergic agents and can treat various CNS disorders. They are use useful in treating sleep disorders and other conditions related to circadian rhythms.

21 Claims, No Drawings

MELATONERGIC INDANYL PIPERAZINES

This application is a continuation-in-part of U.S. Ser. No. 08/458,925 filed on Jun. 2, 1995 now abandoned.

BACKGROUND OF THE INVENTION

The invention deals with indanyl-substituted piperazines, also known in the literature as 1-(2,3-dihydro-1H-inden-1-yl)piperazines, which have bioaffecting properties and to their preparation, formulation and use. Specifically, the invention is concerned with highly water soluble piperazines having substituted indanyl moieties attached to one nitrogen of the piperazine ring. These compounds are useful melatonergic agents because they are $ML_1$ receptor agonists and partial agonists. They have potential activity as sedatives, for treating sleep-related disorders and for treating anxiety, depression and various CNS disorders related to circadian rhythms.

Melatonin, i.e., N-acetyl-5-methoxytryptamine, is a hormone which is synthesized and secreted primarily by the pineal gland. In mammals, melatonin levels show a cyclical, circadian pattern, with with highest levels occurring during the dark period of a circadian light-cark cycle. Melatonin appears to modulate a variety of neural and endocrine functions in vertebrates, including the regulation of reproduction, the control of circadian rhythms and the modulation of retinal physiology.

Melatonin binding sites have been found in several diverse tissues of the body—i.e., in the retina, superchiasmatic nucleus, spleen, etc. Thus, melatonin exerts multiple physiological effects, is not highly selective, and has a potential for producing unwanted side effects. Melatonin agonists should be more selective than melatonin and give fewer side effects, resulting in products having more predictable activity.

The melatonin antagonist, luzindole, exhibits antidepressant-like effects. See Dubocovich et al, *European Journal of Pharmacology* 182, (1990), pages 313–325. Luzindole binds to human melatonin receptors. Like luzindole, compounds of this invention bind to these receptors and, therefore, are believed to have antidepressant character.

Certain compounds of the invention are structurally related to compounds disclosed as intermediates in Manoury, et al., U.S. Pat. No. 4,963,680. See Examples 2 through 5 of the patent. However, the compounds of the '680 patent are not taught as having therapeutic activity of their own. They are only discussed as chemical intermediates in processes for making chemically distinct compounds which are therapeutic agents.

90-242933/32, EISA 22.12.88, JO 2169-569-A shows cyclic amine derivatives for the treatment or prophylaxis of senile dementia, cerebral apoplexy, cerebral atherosclerosis, traumatic cerebral damage, post cerebral edema, or cerebral palsy. The compounds can be piperidines or piperazines linked to carboxamide groups and to heterocyclic rings. 89-001045/01, EISA 22.06.87, EP 296-560-A shows similar compounds having selective antiacetylcholinesterace activity.

89-074668/10, TAIY-24.07.87, JO 1029-310-A shows asthma medicaments of formula i:

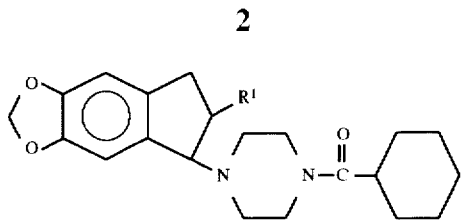

wherein $R_1$ is lower alkyl.

88-272140/39, TAIY-27.03.83, EP-283-551-A deals with drugs for amelioration of cerebral circulation and metabolism which are indene derivatives of formula ii:

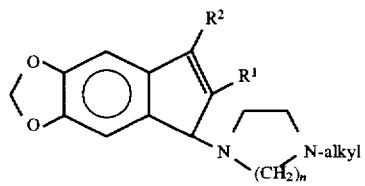

wherein $R_1$ is lower alkyl, $R_2$ is H, aryl, or lower alkyl and n is 2 or 3.

88-046878/07, TAIY-26.06.86, J6 3005-063-A refers to indanes used to treat bronchial asthma. The compounds are of formula iii:

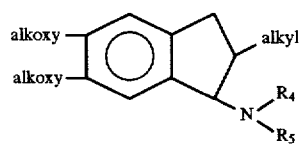

In formula ii, $R_4$ and $R_5$ may form, with the N atom, or piperidinyl, piperazinyl, or homopiperazinyl group.

U.S. Pat. No. 4,983,607 to Manoury, et al., discusses quinolinone derivatives which possess high affinity for "$5\text{-HT}_{1A}$ type serotoninergic receptors".

The structurally related compound 1-(2,3-dihydro-6-methoxy-1H-inden-1-yl)-1-homopiperazine is disclosed in Example 2 of U.S. Pat. No. 4,963,680.

WO 92/10192 of Bogeso, et al., shows compounds of formula iv:

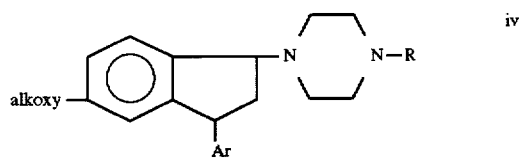

wherein Ar is an optionally substituted phenyl, thiophene or furan ring; and R can be hydrogen, alkyl, alkenyl, cycloalkyl, or cycloalkyl-substituted alkyl.

In addition, indanyl and tetralinyl-piperazines have been disclosed as useful therapeutic agents in a variety of patents, such as: U.S. Pat. No. 5,010,079; WO 9322293-A1; EP 49772-A1; WO 9316057; EP 35363; EP 354093A; EP354094A; and WO 9210292. For example, compounds of general formula vi are claimed in EP 183,349A1, as potent $5\text{-HT}_2$ antagonists useful in treatment of cardiovascular diseases including hypertension and anxiety.

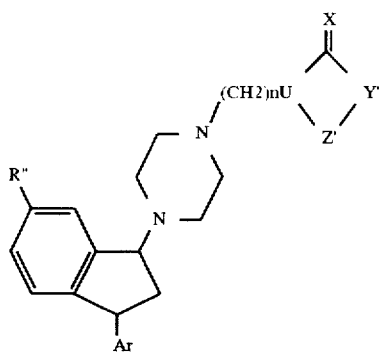
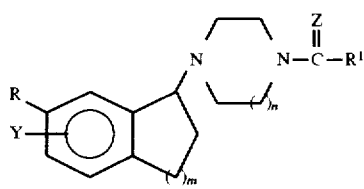

Also disclosed therein is the preparation of these compounds via Method a (below) by alkylation of a substituted or unsubstituted piperazine with a halo- or alkanesulfonyl-indane (III) to give the key intermediate, IV. The intermediate, III, is prepared from the corresponding indanones, II, by reduction of the ketone and subsequent conversion of the resulting alcohol to a halo- or alkanesulfonyl leaving group. One problem with this multi-step method is that conditions must be rigorously controlled to prevent the elimination of HX from the halo- or alkanesulfonyl-indane (III) to give the undesired indene byproduct, V, during both steps of this procedure.

Method a is:

wherein:

R is H, $C_{1-4}$ alkyl, or $C_{1-9}$ alkoxy;
Y is hydrogen, $C_{1-4}$ alkoxy, or halogen;
Z is O or S;
m is 1 or 2;
n is 1 or 2; and
$R^1$ is $C_{1-6}$ alkyl (straight or branched), $C_{1-6}$ haloalkyl, $C_{1-4}$ alkoxy, $C_{1-4}$ thioalkoxy, $C_{1-4}$ thioalkoxy substituted $C_{1-4}$ alkyl, $C_{1-6}$ alkoxy substituted $C_{1-4}$ alkyl, $C_{2-20}$ alkenyl (straight or branched), $C_{3-6}$ cycloalkyl, phenyl, thienyl, pyrrolyl, furanyl, thiadiazolyl, indolyl, or $NR^2R^3$ wherein $R^2$ and $R^3$ are independently hydrogen, $C_{1-3}$ alkyl or $C_{3-6}$ cycloalkyl.

Pharmaceutically acceptable salts, solvates or mixtures of these compounds can be used.

The compounds of the invention are advantageous in several ways. They have melatonergic and other CNS properties and are believed useful as agents for the treatment of stress, sleep disorders, seasonal depression, appetite

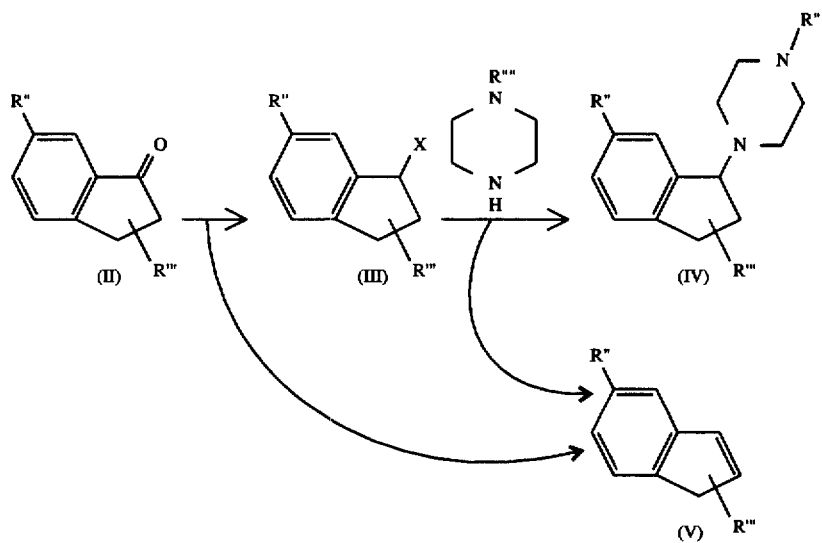

All of the publications cited in the last four paragraphs use synthetic strategies similar to Method a.

SUMMARY AND DETAILED DESCRIPTION OF THE INVENTION

In its broadest aspect, the invention is concerned with indanyl piperazines having useful melatonergic properties, their preparation, and methods and compositions which employ them.

The compounds of the invention are those of formula I and pharmaceutically acceptable salts thereof. Formula I is:

regulation, shifts in circadian cycles (e.g. jet lag), melancholia and the like.

In addition, they are highly water soluble, penetrate the blood-brain barrier well and have long biological half-lives. Their physical and pharmacological properties make them excellent candidates for delivery via oral dosage forms.

In Formula I, R is H, $C_{1-4}$ alkyl or $C_{1-9}$ alkyloxy.
Y may be hydrogen, $C_{1-4}$ alkyloxy or halogen.
Z is O or S.
m is 1 or 2.
n is 1 or 2, with compounds in which n is 1 being preferred.

$R^1$ is $C_{1-6}$ alkyl (straight or branched), $C_{1-6}$ haloalkyl, $C_{1-4}$ alkoxy, $C_{1-4}$ thioalkoxy, ($C_{1-4}$ thioalkoxy) $C_{1-4}$ alkyl, ($C_{1-6}$ alkoxy) $C_{1-4}$ alkyl, $C_{2-20}$ alkenyl (straight or branched), $C_{3-6}$ cycloalkyl, phenyl, thienyl, pyrrolyl, furanyl, thiadiazolyl, indolyl, or $NR^2R^3$ wherein $R^2$ and $R^3$ are independently hydrogen, $C_{1-3}$ alkyl or $C_{3-6}$ cycloalkyl.

By "alkyl" applicants mean straight or branched saturated acyclic moieties containing the indicated number of carbon atoms. In this disclosure, "Me", "Et", "n-Pr", "i-Pr", and "c-Pr" refer to $CH_3$—, $CH_3CH_2$—, $CH_3CH_2CH_2$—, $(CH_3)_2CH$—, and

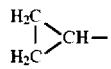

groups, respectively.

When using "haloalkyl", applicants mean alkyl groups bearing from one to three substituents selected from Br, Cl, F or I.

The term "alkoxy" refers to alkyloxy or —O-alkyl moieties.

By "alkenyl" is meant straight or branched moieties having from 2 to 4 carbon atoms and containing one site of ethylenic unsaturation.

The term "cycloalkyl" refers to saturated cyclic groups conforming to the formula $C_xH_{(2x-1)}$ and containing from 3 to 5 carbon atoms.

"$NR^2R^3$" refers to monoalkyl- and dialkyl-amino groups wherein $R^2$ and $R^3$ are independently hydrogen, or noncyclic, straight, or branched $C_{1-4}$ alkyl or $C_{3-5}$ cycloalkyl moieties. Groups wherein $R^2$ is straight or branched $C_{1-4}$ alkyl and $R^3$ is hydrogen are preferred.

By "halogen" is meant bromine, chlorine, fluorine or iodine substituents.

When $R^1$ is a group containing a cycloalkyl, phenyl, furanyl, thienyl, pyrrolyl or indolyl ring, one or more ring substituent(s) can be present. Suitable ring substituents are: alkyl (preferably methyl), hydroxyl, or halogen (preferably one or two bromine or chlorine atoms). Thus, $R^1$ may be chlorophenyl, hydroxyphenyl, bromofuranyl, methylfuranyl, methyl cyclohexyl, bromo- or chlorothienyl, dibromothienyl and the like.

In chemical terms herein, "indane," "indanyl," "tetralin," and "tetralinyl" refer respectively to "2,3-dihydro-1 H-indene," and "2,3-dihydro-1H-inden-1-yl," "1,2,3,4-tetrahydronaphthalene," and "1,2,3,4-tetrahydronaphthalen-1-yl."

Compounds of Formula I also encompass all pharmaceutically acceptable acid addition salts thereof. The pharmaceutically acceptable acid additions salts of the invention are those in which the counter-ion does not contribute significantly to the toxicity or pharmacological activity of the salt and, as such, they are the pharmacological equivalents of the bases of Formula I. They are generally preferred for medical usage. In some instances, they have physical properties which make them more desirable for pharmaceutical formulations. Such properties include solubility, lack of hygroscopicity, compressibility with respect to tablet formation and compatibility with other ingredients with which the substance may be used for pharmaceutical purposes. Salts of piperazines are highly water soluble.

The salts are routinely made by admixture of a Formula I base with the selected acids, preferably by contact in solution employing an excess of commonly used inert solvents, such as water, ether, benzene, methanol, ethanol, ethyl acetate, acetone, and acetonitrile. They may also be made by metathesis or treatment with an ion exchange resin under conditions in which the anion of one salt of the substance of Formula I is replaced by another anion under conditions which permit separation of the desired species, such as by precipitation from solution or extraction into a solvent, or elution from or retention on an ion exchange resin.

Pharmaceutically acceptable acids for the purposes of salt formation of the substances of Formula I include fumaric, sulfuric, phosphoric, hydrochloric, hydrobromic, hydroiodic, citric, acetic, benzoic, cinnamic, mandelic, phosphoric, nitric, mucic, isethionic, palmitic, heptanoic, and the like.

Additionally, compounds of Formula I also encompass all pharmaceutically acceptable solvates, hydrates being preferred solvates. The present invention also includes both geometrical isomers and optical isomers, e.g., mixtures of enantiomers as well as individual enantiomers and diastereomers, which arise as a consequence of structural asymmetry in certain compounds of the instant series. In general, (–)-enantiomers are preferred. Separation or stereospecific syntheses of the individual isomers is accomplished by application of various methods which are well known to practitioners in the art. Descriptive details of the synthesis of compounds of Formula I and of intermediates appears below.

The compounds of the present invention have affinity for human receptors of the endogenous pineal hormone, melatonin, as determined in a functional assay. The biological testing is described herein below.

As has been discussed above, melatonin is involved in the regulation of a variety of biological rhythms and exerts its biological effects via interaction with specific receptors. There is evidence that administration of melatonin agonists is of clinical utility in the treatment of various conditions regulated by melatonin. Such conditions include depression, jet-lag, work-shift syndrome, sleep disorders, glaucoma, some disorders associated with reproduction, cancer, immune disorders and neuroendocrine disorders.

The systemic administration and dosing regimen of compounds of Formula I can be done in a manner similar to that described for melatonin itself. The dosage and dosage regimen must be adjusted using sound professional judgment and taking into account such variables as the age, body weight, sex and physical condition of the recipient, the route of administration and the nature of the illness being treated.

Preferred classes of compounds of Formula I include those in which R is methoxy, m and n are 1, Y is H, Z is O or S, and $R^1$ is $C_{1-4}$ alkyl, $C_{3-6}$ cycloalkyl, thienyl, furanyl, and $NHR^2$, with $R^2$ being straight or branched $C_{1-4}$ alkyl. Salts of these are also useful.

The preferred compounds include:
1-(Cyclopropylcarbonyl)-4-(6-methoxy-indan-1-yl) piperazine;
1-Butanoyl-4-(6-methoxy-indan-1-yl)piperazine;
1-(Cyclobutylcarbonyl)-4-(6-methoxy-indan-1-yl) piperazine;
4-(6-Methoxy-indan-1-yl)-1-(2-methyl-propanoyl) piperazine;
1-[(1-Methyl-ethenyl)carbonyl]-4-(6-methoxy-indan-1-yl) piperazine;
(–)-1-(Cyclopropylcarbonyl)-4-(6-methoxy-indan-1-yl) piperazine;
(–)-4-(6-Methoxy-indan-1-yl)-1-(2-methyl-propanoyl) piperazine;
(–)-4-(6-Methoxy-indan-1-yl)-1-(2-methylthioacetyl) piperazine;
1-(Cyclopropylcarbonyl)-4-(6-ethoxy-indan-1-yl) piperazine;
4-(6-Methoxy-indan-1-yl)-1-propanoylpiperazine;
1-(Cyclopentylcarbonyl)-4-(6-methoxy-indan-1-yl) piperazine;

1-(Ethenylcarbonyl)-4-(6-methoxy-indan-1-yl)piperazine;
4-(6-Methoxy-indan-1-yl)-1-(2-methyl-propanoyl) homopiperazine;
1-(Cyclopropylcarbonyl)-4-(6-methoxy-indan-1-yl) homopiperazine;
1-(2,2-dimethyl-propanoyl)-4-(6-methoxy-indan-1-yl) piperazine;
1-(Methoxyacetyl)-4-(6-methoxy-indan-1-yl)piperazine;
(−)-1-|(2,2-Dimethyl-ethenyl)carbonyl|-4-(6-methoxy-indan-1-yl)piperazine;
(−)-1-(Chloroacetyl)-4-(6-methoxy-indan-1-yl)piperazine;
4-(6-Methoxy-indan-1-yl)-1-(2-methyl-butanoyl) piperazine;
(−)-1-(2,2-Dimethyl-butanoyl)-4-(6-methoxy-indan-1-yl) piperazine;
(−)-4-(6-Methoxy-indan-1-yl)-1-(2-oxo-butanoyl) piperazine;
1-(Cyclopropylcarbonyl)-4-|6-(1-propyloxy)indan-1-yl| piperazine;
1-(Cyclopropylcarbonyl)-4-(5-fluoro-6-methoxy-indan-1-yl)piperazine;
4-(5-Fluoro-6-methoxy-indan-1-yl)-1-(2-methylpropanoyl) piperazine;
1-Acetyl-4-(6-methoxy-indan-1-yl)piperazine;
4-(6-Methoxy-indan-1-yl)-1-(2-methyl-propanoyl) piperazine;
1-(Cyclopropylcarbonyl)-4-(indan-1-yl)piperazine;
(−)-1-|(1-Methylcyclohexyl)carbonyl|-4-(6-methoxy-indan-1-yl)piperazine;
(−)-4-(6-Methoxy-indan-1-yl)-1-(10-undecenoyl) piperazine;
(−)-4-(6-Methoxy-indan-1-yl)-1-(4-pentenoyl)piperazine;
1-(Cyclopropylcarbonyl)-4-(6-nonyloxy-indan-1-yl) piperazine;
1-(Cyclopropylcarbonyl)-4-(6-ethyl-indan-1-yl)piperazine;
4-(6-Ethyl-indan-1-yl)-1-(2-methylpropanoyl)piperazine;
4-(6-Methoxy-indan-1-yl)-1-|(2-thienyl)carbonyl| piperazine;
1-|(2-Furanyl)carbonyl|-4-(6-methoxy-indan-1-yl) piperazine;
(−)-4-(6-Methoxy-indan-1-yl)-1-[(2-thienyl)carbonyl] piperazine;
(−)-1-|(2-Furanyl)carbonyl|-4-(6-methoxy-indan-1-yl) piperazine;
(−)-4-(6-Methoxy-indan-1-yl)-1-[(3-methyl-furan-2-yl) carbonyl|piperazine;
(−)-4-(6-Methoxy-indan-1-yl)-1-|(1-methyl-pyrrol-2-yl) carbonyl|piperazine;
(−)-4-(6-Methoxy-indan-1-yl)-1-[(1-methyl-thien-2-yl) carbonyl|piperazine;
(−)-4-(6-Methoxy-indan-1-yl)-1-[(3-thienyl)carbonyl| piperazine;
(−)-1-|(3-Chlorothien-2-yl)carbonyl|-4-(6-methoxy-indan-1-yl)-1-piperazine;
(−)-1-|(3-Bromothien-2-yl)carbonyl|-4-(6-Methoxy-indan-1-yl)piperazine;
(−)-1-(2-Hydroxybenzoyl)-4-(6-methoxy-indan-1-yl) piperazine;
(−)-1-|(3-Furanyl)carbonyl|-4-(6-methoxy-indan-1-yl) piperazine;
(−)-4-(6-Methoxy-indan-1-yl)-1-|(1H-pyrrol-2-yl)carbonyl| -piperazine;
(−)-4-(6-Methoxy-indan-1-yl)-1-|(1,2,3-thiadiazol-4-yl) carbonyl|-piperazine;
(−)-1-|(5-Bromo-furan-2-yl)carbonyl|-4-(6-methoxy-indan-1-yl)piperazine;
(−)-1-(Benzoyl)-4-(6-methoxy-indan-1-yl)piperazine;
(−)-1-|(1H-indol-3-yl)carbonyl|-4-(6-methoxy-indan-1-yl) piperazine;
(−)-1-|(4,5-Dibromo-thien-2-yl)carbonyl|-4-(6-methoxy-indan-1-yl)piperazine;
(−)-1-(2-Chlorobenzoyl)-4-(6-methoxy-indan-1-yl) piperazine;
(−)-1-|(5-Chloro-thien-2-yl)carbonyl|-4-(6-methoxy-indan-1-yl)piperazine;
1-(Ethoxycarbonyl)-4-(6-methoxy-indan-1-yl)piperazine;
N-Cyclopropyl-4-(6-methoxy-indan-1-yl)piperazine-1-carboxamide;
N-Methyl-4-(6-methoxy-indan-1-yl)piperazine-1-carboxamide;
(−)-N-Ethyl-4-(6-methoxy-indan-1-yl)piperazine-1-carboxamide;
N-Cyclopropyl-4-(6-methoxy-indan-1-yl)piperazine-1-carboxamide;
N-(n-Propyl)-4-(6-methoxy-indan-1-yl)piperazine-1-carboxamide;
N-Ethyl-4-(6-methoxy-indan-1-yl)piperazine-1-carboxamide;
N-Ethyl-4-(6-methoxy-indan-1-yl)homopiperazine-1-carboxamide;
N-(1-Methylethyl)-4-(6-methoxy-indan-1-yl)piperazine-1-carboxamide;
N,N-Dimethyl-4-(6-methoxy-indan-1-yl)piperazine-1-carboxamide;
N-Ethyl-4-(6-ethoxy-indan-1-yl)piperazine-1-carboxamide;
N-Ethyl-4-(6-propyloxy-indan-1-yl)piperazine-1-carboxamide;
N-Ethyl-4-(6-nonyloxy-indan-1-yl)piperazine-1-carboxamide;
N-Ethyl-4-(5-fluoro-6-methoxy-indan-1-yl)piperazine-1-carboxamide;
N-Methyl-4-(5-fluoro-6-methoxy-indan-1-yl)piperazine-1-carboxamide;
1-Acetyl-4-(7-methoxy-tetralin-1-yl)piperazine;
1-(1-Butanoyl)-4-(7-methoxy-tetralin-1-yl)piperazine;
1-(Cyclopropylcarbonyl)-4-(7-methoxy-tetralin-1-yl) piperazine;
N-Methyl-4-(7-methoxy-tetralin-1-yl)piperazine-1-carboxamide; and
N-Ethyl-4-(7-methoxy-tetralin-1-yl)piperazine-1-carboxamide.

Compounds of Formula I and their salts can be prepared using the processes shown in the following scheme(s):

SCHEME 1:
Preferred Synthesis of Compounds of Formula I

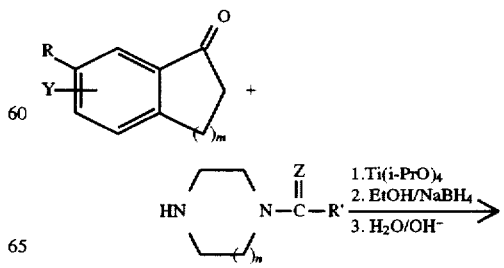

SCHEME 1:
Preferred Synthesis of Compounds of Formula I
-continued

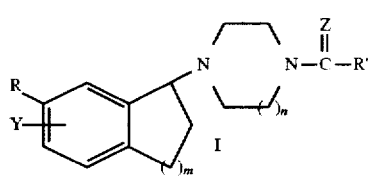

SCHEME 2:
Synthesis of Piperazine Intermediates

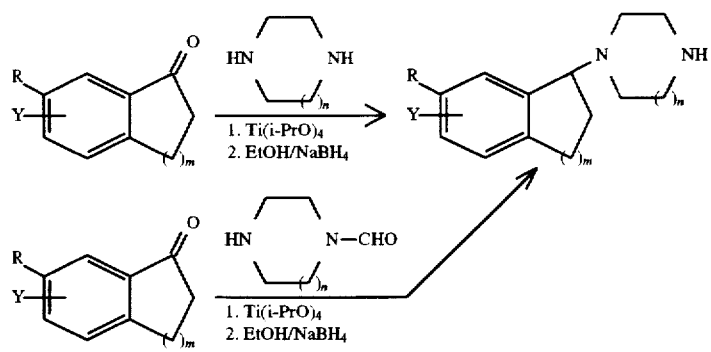

SCHEME 3:
Synthesis of Piperazine Derivatives of Formula I

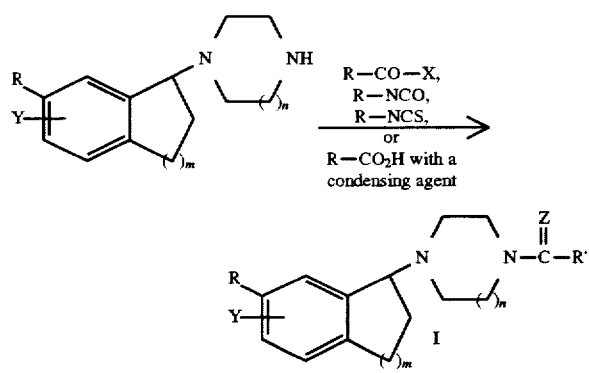

The most preferred route (Scheme 1) to the compounds of Formula I comprises a modification of the titanium(IV) isopropoxide reductive amination procedure described by R. J. Mattson, et al. [*J. Organic Chemistry* 55 2553 (1990)]. In this method (Scheme 1) an acyl-piperazine is reductively coupled with the substituted ketone to give the products, I, directly in one step.

Alternatively, the substituted ketone can be condensed (Scheme 2) with either piperazine or more preferably with 1-formyl-piperazine to give the indanyl-piperazine intermediate. The 1-formyl-piperazine negates the need for the large excess of piperazine and is cleanly hydrolyzed during the work up to give the indanyl-piperazine intermediate. This intermediate can then be acylated (Scheme 3) using standard methods to give the products of Formula I.

These processes may be adapted in order to produce other compounds embraced by the invention, but not specifically disclosed herein. Variations of these methods to produce compounds via different, but conventional, routes will be evident to one skilled in the art. Representative examples are set out in "Description of Specific Embodiments" section, below.

The compounds of Formula I and their salts are melatonergic agents. Their melatonergic activity has been demonstrated via receptor binding studies using human melatonin receptors as set out in Example 21.

The compounds of the invention may be administered to patients in need of melatonergic treatment in a variety of ways. Thus oral, transdermal, subcutaneous, intravenous, intramuscular, rectal, buccal, intranasal and ocular routes can be used.

One or more of the compounds of the invention is mixed with pharmaceutically suitable amounts of one more conventional pharmaceutical excipients to produce a formulation to be administered by the desired route. Generally, such formulations will contain one or several carriers or diluents. Useful carriers include solids, semi-solids, and liquids which have miscibility, or other compatability, with the active agents(s) so the they can efficiently deliver same to a patient or other host.

Suitable carriers include lactose, dextrose, sucrose, sorbitol, mannitol, starches, gum acacia, calcium phosphate, alginates, tragacanth, gelatin, calcium silicate, microcrystalline cellulose, polyvinyl pyrrolidone, cellulose, water, syrup, methyl cellulose, methyl- and propyl-hydroxybenzoates, talc, magnesium stearate, mineral oil and the like. Mixtures are operable.

Other useful excipients include, lubricants, wetting agents, gellants, emulsifiers, preservatives, colorants, perfumes, flavor enhancers, drying agents and the like. Mixtures can be employed.

Generally, compositions which include the compounds of the invention will contain from about 0.10 to about 10% by weight of active compound(s) and 99.9 to 90% by weight, or other suitable amounts, of excipients(s).

Dosage levels will be dictated by the patient's needs and by the medical judgment of the treating physician. Generally, however, dosages of about 0.1 to about 100 mg per day are useful to treat sleep disorders or other disorders related to circadian rhythm.

While human patients are preferred, the compounds of the invention may be used to treat other subjects, i.e., animals, preferably mammals.

DESCRIPTION OF SPECIFIC EMBODIMENTS

The compounds of the invention, their preparation and their biological properties will be more clearly understood upon consideration of the following examples. The examples are illustrative only and are not intended to limit the scope the invention.

In these examples, temperatures are expressed in degrees Celsius and melting points are uncorrected. The elemental analysis results are reported as percent by weight. All percentages are, unless less designated otherwise, weight percent based on total composition weight.

EXAMPLES

PREPARATION OF INTERMEDIATES

The following examples illustrate the process of making piperazine and homopiperazine intermediates.

Example 1

(6-Methoxyindan-1-yl)piperazine

Method A

Step 1: An intimate mixture of 6-methoxy-1-indanone (10 g, 62 mmol), piperazine (53 g, 620 mmol) and titanium(IV) isopropoxide (17.6 g, 124 mmol) was heated on the steam bath for 10 minutes (step 1). The IR spectrum of the mixture showed no carbonyl absorption.

Step 2: The material was dissolved in ethanol and sodium borohydride added (2.5 g, 62 mmol). After stirring for 1 hr the solution was heated to reflux.

Step 3: When a solution had occurred 15% NaOH solution (50 ml) was added. The insoluble material was filtered and discarded. The solution was concentrated in vacuo and the residue dissolved in ether. The solution was washed with water and 1N HCl solution. The acid washes were made basic and the mixture was extracted with methylene chloride to give the product, which was converted to the HCl salt in absolute ethanol |beige solid, 13.3 g, 80%, mp: 150°–152° C. (HCl salt)]. Calcd for $C_{14}H_{20}N_2O.HCl.0.5H_2O$: C, 60.52; H, 7.98; N, 10.08. Found: C, 60.59; H, 7.65; N, 10.11.

Method B

Step 1: A mixture of 6-methoxy-indan-1-one (1.6 g, 10 mmol), 1-formyl piperazine (2.3 g, 20 mmol), and titanium (IV) isopropoxide (7 ml, 21 mmol) was heated gently on a steam bath for 10 min. The IR spectrum of the mixture then showed no ketone absorption.

Step 2: The mixture was dissolved in absolute ethanol (20 ml) and sodium borohydride (1.6 g, 40 mmol) was added. The reaction mixture was heated gently on a steam bath for 10 min and then stirred for 16 hr.

Step 3: The reaction was then heated to give a clear solution and then quenched with 15% sodium hydroxide (4 ml) to produce a white precipitate. The mixture was stirred for 1 hr and then filtered. The precipitate was washed thoroughly with ethanol The combined filtrates were concentrated in vacuo and the residue partitioned between diethyl ether and 1N HCl. The aqueous layer was made basic with with sodium carbonate and then extracted with methylene chloride. The extracts were dried over sodium sulfate and concentrated in vacuo to give the product (1.7 g, 73.3%).

Example 2

1-(Indan-1-yl)piperazine

Piperazine (17.2 g, 0.2 mol), indan-1-one (2.6 g, 20 mmol), titanium(IV) isopropoxide (13.3 ml, 40 mmol) and sodium borohydride (3.6 g, 95 mmol) were reacted by Method A to give the product (1.5 g, 37.1%). The crude product was used without purification.

Example 3

1-(6-Ethoxyindan-1-yl)piperazine

Piperazine (19.8 g, 0.23 mol), 6-ethoxyindan-1-one (4.00 g, 23 mmol), titanium(IV) isopropoxide (15.3 ml, 46 mmol) and sodium borohydride (2.7 g, 71 mmol) were reacted by Method A to give the product which was converted to the fumurate salt (beige solid, 5.7 g, 68.5%, mp: 142°–147° C.). Calcd for $C_{15}H_{22}N_2O.C_4H_4O_4$: C, 62.97%; H, 7.23%; N, 7.73%. Found: C, 62.88%; H, 7.22%; N, 7.48%.

Example 4

1-|6-(1-Propyloxy)indan-1-yl|piperazine

Piperazine (20.6 g, 0.24 mol), 6-(1-propoxy)indan-1-one (4.6 g, 24 mmol), titanium(IV) isopropoxide (16 ml, 48 mmol) and sodium borohydride (2.8 g, 74 mmol) were reacted by Method A to give the product which was converted to the fumarate salt (beige solid, 5.0 g, 55.4%, mp: 157°–159° C.). Calcd for $C_{16}H_{24}N_2O.C_4H_4O_4.0.3H_2O$: C, 62.91%; H, 7.55%; N, 7.34%. Found: C, 62.70%; H, 7.45%; N, 7.07%.

Example 5

1-(6-methoxy-indan-1-yl)homopiperazine

Homopiperazine (30.6 g, 0.306 mol), 6-methoxy-indan-1-one (4.95 g, 30.56 mmol), titanium(IV) isopropoxide (17.9 ml, 60 mmol) and sodium borohydride (2.7 g, 71 mmol) were reacted by Method A to give the product (5.3 g, 70.5%). The crude product was used without purification.

Example 6

(6-Ethylindan-1-yl)piperazine

Step 1. 4-Ethyl cinnamic acid

A solution of 4-ethylbenzaldehyde (26.0 g, 0.2 mol), malonic acid (41.6 g, 0.4 mol), pyrrolidine (3 ml), and pyridine (80 ml) was heated in an 85° C. oil bath for 16 hr. The reaction mixture was poured over crushed ice (800 ml), and then made acidic with 12N HCl (100 ml). The white precipitate was filtered, suspended in 1N HCl, and filtered again. The white precipitate was washed with water and air dried to give 4-ethyl cinnamic acid (34.0 g, 96.6).

Step 2. 3-(4-Ethylphenyl)propionic acid

An ethanol (250 ml) solution of 4-ethyl cinnamic acid (34.0 g, 0.191 mol) was hydrogenated at 60 psi over 10% Pd/C (2 g) for 2 hr. The mixture was filtered and concentrated in vacuo to give 3-(4-ethylphenyl)propionic acid as a white solid (34 g, 100%).

Step 3. 6-Ethyl-1-indanone

A mixture of 3-(4-ethylphenyl)propionic acid (34 g, 0.191 mol) and thionyl chloride (70 ml), and $CH_2Cl_2$ (100 ml) was heated to reflux for 30 min. The resulting solution was concentrated in vacuo to a light brown oil. This oil was added slowly to an ice bath cooled mixture of $AlCl_3$ (33.1 g, 0.248 mole) in $CH_2Cl_2$ (75 ml). The mixture was stirred for 15 min and then heated to reflux for 45 min. The mixture was cooled and poured over crushed ice (200 ml) and 12N HCl (100 ml). The $CH_2Cl_2$ layer was separated, washed with 3N HCl, saturated $Na_2CO_3$, water, and brine. The $CH_2Cl_2$ layer was concentrated in vacuo and Kúigelrohr distilled to a clear oil (27.4 g, 89%). $^1$H-NMR ($CDCl_3$, 300 MHz) δ1.23 (t, 3H, J=7.5 Hz), 2.65–2.72 (m, 4H), 3.07 (t, 2H, J=5.9 Hz), 7.36 (d, 1H, J=8.1 Hz), 7.41 (d, 1H, J=8.1 Hz), 7.57 (s, 1H).

Step 4. (6-Ethylindan-1-yl)piperazine

This compound, prepared from 6-ethyl-1-indanone, piperazine and titanium isopropoxide as described in method B above, was isolated as the fumarate salt (50%, mp 151°–153° C.). Calc'd for $C_{15}H_{22}N_2.C_4H_4O_4$: C, 65.87%; H, 7.57%; N, 8.09%. Found: C, 65.59%; H, 7.50%; N, 8.00%.

Example 7

1-(5-fluoro-6-methoxy-indan-1-yl)piperazine

3-Fluoro-4-methoxybenzaldehyde was converted to 5-fluoro-6-methoxy-1-indanone by method 2, steps 1–4 above, (92%, mp 149°–151° C.). Anal. Calc'd for $C_{10}H_9FO_2$: C, 66.66%; H, 5.03%. Found: C, 66.65%; H, 4.96%.

1-Formyl-piperazine (2.1 g, 20 mmol), 5-fluoro-6-methoxy-indan-1-one (1.8 g, 10 mmol), titanium(IV) isopropoxide (5 ml, 15 mmol), and sodium borohydride (1.2 g, 30 mmol) were reacted by Method B to give the product (2.2 g, 88%, mp 163°–166° C.). Calcd for $C_{14}H_{19}FN_2O \cdot C_4H_4O_4 \cdot 0.1H_2O$: C, 56.23%; H, 6.56%; N, 7.28%. Found: C, 56.65%; H, 6.41%; N, 6.98%.

Example 8

1-[6-(1-nonyloxy)indan-1-yl]piperazine
Step 1. 6-(1-Nonyloxy)-1-indanone

A solution of 6-hydroxy-1-indanone (0.9 g, 6 mmol), NaOH (6 mL 1N sol'n, 6 mmol) and 1-bromononane (1.4 g, 6.6 mmol) in ethanol (50 mL) was heated at reflux for 14 h and the solution concentrated in vacuo. The residue was dissolved in ether and the solution washed with 1N NaOH solution. The ether layer was dried and purified by chromatography on silica eluting with ethyl acetate-hexane (1:9) to give the product, (67%, mp: 41°–42° C.). $C_{18}H_{26}O_2$: C, 78.79%; H, 9.55%. Found: C, 78.69%; H, 9.44%.
Step 2. 1-[6-(1-Nonyloxy)indan-1-yl]piperazine Piperazine (4.4 g, 51 mmol), 6-(1-nonyloxy)indan-1-one (1.4 g, 5.1 mmol), titanium(IV) isopropoxide (2.5 ml, 7.5 mmol) and sodium borohydride (1.8 g, 47 mmol) were reacted by Method B to give the product (1.6 g, 91.2%, mp: 138°–144° C.). Calcd for $C_{22}H_{36}N_2O \cdot C_4H_4O_4 \cdot 0.4H_2O$: C, 66.75%; H, 8.79%; N, 5.99%. Found: C, 66.76%; H, 8.71%; N, 5.90%.

Example 9

(7-Methoxytetralin-1-yl)piperazine

This compound, prepared from 7-methoxy-tetralin-1-one, piperazine, and titanium(IV) isopropoxide as described in method B above, was isolated as the fumarate salt (58%, mp: 185°–186° C.). Calc'd for $C_{15}H_{22}N_2O \cdot C_4H_4O_4$: C, 62.97%; H, 7.23%; N, 7.73%. Found: C, 63.02%; H, 7.31; N, 7.63%.

Example 10

Resolution of (6-methoxy-indan-1-yl)piperazine.

A mixture of (6-methoxy-indan-1-yl)piperazine (2.3 g, 10 mmol) and (1S)-(+)-10-camphorsulfonic acid (2.3 g, 10 mmol) was recrystallized from ethanol-water until the crystal attained a constant melting point yielding (−)-(6-methoxy-indan-1-yl)piperazine (1S)-10-camphorsulfonic acid salt (22%, mp: 234.5°–234° C., $|\alpha|^{25}_D$–36.3°). Calc'd for $C_{14}H_{20}N_2O_2 \cdot C_{10}H_{10}O_4S$: C, 62.04%; H, 7.81%; N, 6.03%. Found: C, 62.01%; H, 7.96; N, 5.97%.

A sample (0.2 g, 0.43 mmol) of the above salt was suspended in water and the mixture made basic with 1N NaOH. The basic solution was extracted with $CH_2Cl_2$. The extracts were then dried and concentrated in vacuo. NMR analysis of this free base using a chiral shift solution showed none of the enantiomeric compound. A solution of fumaric acid (49 mg) in methanol was added, the solution concentrated in vacuo and the residue crystallized to give the fumarate salt, (mp: 170°–172° C., $|\alpha|^{25}_D$–72.3°). Calc'd for $C_{14}H_{20}N_2O_2 \cdot C_4H_4O_4$: C, 62.05%; H, 6.94%; N, 8.04%. Found: C, 62.08%; H, 6.61%; N, 8.26%.

General Procedure for Preparation of Amides, Urethanes, and tertiary-Ureas of Formula I

Example 11

1-Cyclopropylcarbonyl-4-(6-methoxy-indan-1-yl)piperazine

A mixture of (6-methoxy-indan-1-yl)piperazine (3.0 g, 15.5 mmol), cyclopropane-carbonyl chloride (1.6 g, 15.5 mmol), and excess powdered potassium carbonate was stirred for 6 hr. The insoluble material was removed and the solution concentrated in vacuo. The residue was dissolved in ether and washed with 1N HCl. The acid washes were made basic with NaOH solution and the mixture was extracted with methylene chloride. The extracts were dried and concentrated in vacuo. The residue was converted to the hydrochloride salt with ethereal HCl to give a solid (75%, mp: 187°–188° C.). Calc'd for $C_{18}H_{24}N_2O_2 \cdot HCl$: C, 64.18%; H, 7.48%; N, 8.32%. Found: C, 63.96%; H, 7.18%; N, 8.18%.

Example 12

1-Acetyl-4-(7-methoxy-tetralin-1-yl)piperazine

This compound was prepared from (7-methoxytetralin-1-yl)piperazine and acetyl chloride by the method described in Example 11 above (pale yellow oil, 58%). Calc'd for $C_{17}H_{24}N_2O_2$: C, 69.93%; H, 8.43%; N, 9.60%. Found: C, 69.94%; H, 8.18%; N, 9.45%.

Table 1 lists other compounds of Formula I prepared by the above method.

TABLE 1

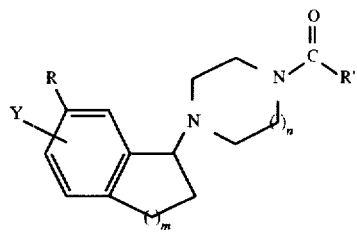

| R | Y | R' | m | n | salt | mp °C. | %C Calc | %H Calc | %N Calc | %C Found | %H Found | %N Found |
|---|---|---|---|---|---|---|---|---|---|---|---|---|
| H | H | -c-Pr | 1 | 1 | — | oil | 73.76 | 7.99 | 10.00 | 74.12 | 8.13 | 10.09 |
| MeO— | H | -i-Pr | 1 | 1 | C₄H₄O₄.0.4 H₂O | 126–128 | 62.07 | 7.29 | 6.58 | 62.44 | 7.08 | 6.18 |
| MeO— | H | —Et | 1 | 1 | C₄H₄O₄ | 115–116 | 62.36 | 6.98 | 6.93 | 62.09 | 6.76 | 6.74 |
| MeO— | H | -n-Pr | 1 | 1 | C₄H₄O₄.0.2 H₂O | 144–145 | 62.60 | 7.26 | 6.64 | 62.39 | 6.96 | 6.44 |
| MeO— | H | -t-Bu | 1 | 1 | C₄H₄O₄ | 175–176 | 63.87 | 7.46 | 6.48 | 63.48 | 7.00 | 6.29 |
| MeO— | H | -c-Bu | 1 | 1 | C₄H₄O₄ | 137–138 | 64.17 | 7.02 | 6.51 | 64.45 | 6.63 | 6.30 |
| MeO— | H | -c-Pent | 1 | 1 | C₄H₄O₄.0.2 H₂O | 127–129 | 64.32 | 7.29 | 6.25 | 64.10 | 6.97 | 6.02 |
| MeO— | H | —CH=CH₂ | 1 | 1 | C₄H₄O₄ | 141–143 | 62.67 | 6.51 | 6.96 | 62.38 | 6.41 | 6.78 |
| MeO— | H | —C(Me)=CH₂ | 1 | 1 | C₄H₄O₄.0.2 H₂O | 170–172 | 62.96 | 6.82 | 6.67 | 62.68 | 6.58 | 6.62 |
| MeO— | H | -2-Thienyl | 1 | 1 | C₄H₄O₄ | 152–154 | 60.25 | 5.72 | 6.11 | 60.26 | 5.62 | 5.91 |
| MeO— | H | -2-Furanyl | 1 | 1 | C₄H₄O₄ | 145–147 | 62.43 | 5.92 | 6.33 | 62.15 | 5.96 | 6.31 |
| EtO— | H | -c-Pr | 1 | 1 | C₄H₄O₄.0.1 H₂O | 169–170 | 63.90 | 7.04 | 6.48 | 63.72 | 7.08 | 6.45 |
| n-PrO— | H | -c-Pr | 1 | 1 | C₄H₄O₄ | 153–154 | 64.85 | 7.26 | 6.30 | 64.85 | 7.32 | 6.07 |
| MeO— | H | -c-Pr | 1 | 2 | C₄H₄O₄ | 150–154 | 64.17 | 7.02 | 6.51 | 63.77 | 6.91 | 6.42 |
| MeO— | H | -i-Pr | 1 | 2 | C₄H₄O₄ | 179–182 | 63.87 | 7.46 | 6.48 | 63.66 | 7.45 | 6.26 |
| MeO— | H | —Me | 1 | 1 | C₄H₄O₄ | 109–111 | 61.53 | 6.71 | 7.17 | 61.29 | 6.6 | 6.62 |
| MeO— | H | —Ph | 1 | 1 | C₄H₄O₄ | 153–156 | 66.36 | 6.24 | 6.19 | 66.25 | 6.03 | 6.11 |
| MeO— | H | —CH₂CHMe₂ | 1 | 1 | 1.5 C₄H₄O₄ | 151–152 | 61.21 | 6.99 | 5.71 | 61.18 | 6.85 | 5.77 |
| MeO— | H | —CH₂—OMe | 1 | 1 | C₄H₄O₄ | 158–160 | 59.99 | 6.71 | 6.66 | 59.8 | 6.8 | 6.61 |
| MeO— | 5-F | -c-Pr | 1 | 1 | C₄H₄O₄.0.5 H₂O | 154–155 | 59.58 | 6.37 | 6.32 | 59.55 | 6.07 | 5.97 |
| MeO— | 5-F | -i-Pr | 1 | 1 | C₄H₄O₄ | 129–131 | 60.54 | 6.70 | 6.42 | 60.31 | 6.77 | 6.24 |
| Et— | H | -c-Pr | 1 | 1 | C₄H₄O₄.0.5 H₂O | 178–179 | 65.23 | 7.38 | 6.62 | 65.03 | 7.10 | 6.24 |
| Et— | H | -i-Pr | 1 | 1 | C₄H₄O₄ | 170–171 | 66.32 | 7.74 | 6.73 | 66.19 | 7.60 | 6.66 |
| C₉H₁₉O— | H | -c-Pr | 1 | 1 | 0.25 H₂O | 67–68 | 74.86 | 9.79 | 6.72 | 74.79 | 9.7 | 6.81 |
| MeO— | H | -c-Pr | 2 | 1 | 0.5 H₂O | oil | 70.56 | 8.41 | 8.66 | 70.56 | 8.24 | 8.35 |
| MeO— | H | —Me | 2 | 1 | 0.2 H₂O | oil | 69.93 | 8.43 | 9.6 | 69.94 | 8.18 | 9.45 |
| MeO— | H | -n-Pr | 2 | 1 | 0.15 CH₂Cl₂ | oil | 69.88 | 8.67 | 8.52 | 70.07 | 8.38 | 8.6 |
| MeO— | H | —NMe₂ | 1 | 1 | C₄H₄O₄ | 166–167 | 60.13 | 6.97 | 10.02 | 60.10 | 6.89 | 9.63 |
| MeO— | H | —OEt | 1 | 1 | C₄H₄O₄ | 164–166 | 59.99 | 6.71 | 6.66 | 60.25 | 6.7 | 6.46 |

General Procedure for Preparation of Secondary Ureas of Formula I

Example 13

N-Methyl-4-(6-methoxy-indan-1-yl)-1-piperazinecarboxamide

Methyl isocyanate (0.25 g, 3.4 mmol) was added to a solution of (6-methoxy-indan-1-yl)piperazine (0.8 g, 3.4 mmol) in CH₂Cl₂. After stirring for 2 hr. the solution was washed with 1N HCl. The acid washes were made basic with NaOH solution and the mixture extracted with methylene chloride. The extracts were dried and concentrated in vacuo. The fumarate was prepared in methanol to give a solid, (85%, mp: 172°–174° C.). Calc'd for C₁₆H₂₃N₂O₂.C₄H₄O₄: C, 59.25%; H, 6.71%; N, 10.36%. Found: C, 58.92%; H, 6.95%; N, 9.96%

Example 14

N-Ethyl-4-(7-methoxy-tetralin-1-yl)-1-piperazinecarboxamide

This compound was prepared from ethyl isocyanate and 7-methoxytetralin-1-yl)piperazine by the method described in Example 13 above (74%, mp: 141°–143° C.).

Table 2 lists other compounds of Formula I prepared by this method.

TABLE 2

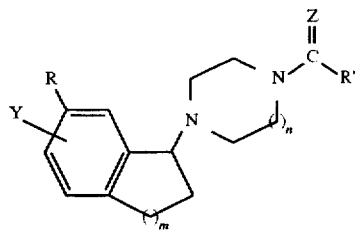

| R | Y | Z | R' | m | n | salt · solvate | mp, °C. | % Calculated C | H | N | % Found C | H | N |
|---|---|---|---|---|---|---|---|---|---|---|---|---|---|
| MeO— | H | O | —NH—Me | 1 | 1 | $C_4H_4O_4$ | 172–174 | 59.25 | 6.71 | 10.36 | 58.92 | 6.95 | 9.96 |
| MeO— | H | O | —NH—Et | 1 | 1 | $C_4H_4O_4 \cdot 0.1\ H_2O$ | 167–168 | 59.87 | 6.99 | 9.97 | 59.65 | 6.91 | 9.81 |
| MeO— | H | O | —NH-n-Pr | 1 | 1 | $C_4H_4O_4$ | 142–144 | 60.96 | 7.21 | 9.69 | 60.64 | 7.04 | 8.94 |
| MeO— | H | O | —NH-i-Pr | 1 | 1 | HCl | 210–211 | 61.09 | 7.97 | 11.87 | 60.57 | 7.87 | 11.58 |
| MeO— | H | O | —NH-c-Pr | 1 | 1 | $C_4H_4O_4$ | 148–149 | 61.24 | 6.77 | 9.74 | 61.18 | 6.85 | 9.61 |
| EtO— | H | O | —NH—Et | 1 | 1 | $C_4H_4O_4$ | 179–181 | 60.96 | 7.21 | 9.69 | 60.59 | 7.31 | 9.89 |
| n-PrO- | H | O | —NH—Et | 1 | 1 | $C_4H_4O_4$ | 165–166 | 61.73 | 7.43 | 9.39 | 61.52 | 7.60 | 9.03 |
| MeO— | H | O | —NH—Et | 1 | 2 | HCl | 205.5–207 | 61.09 | 7.97 | 11.87 | 60.69 | 7.57 | 11.84 |
| $C_9H_{19}O$— | H | O | —NH—Et | 1 | 1 | $C_4H_4O_4 \cdot 0.5\ H_2O$ | 105–113 | 64.42 | 8.58 | 7.77 | 64.51 | 8.62 | 6.98 |
| MeO— | H | O | —NH-n-Pr | 1 | 1 | $C_4H_4O_4$ | 142–144 | 60.96 | 7.21 | 9.69 | 60.64 | 7.04 | 8.94 |
| MeO— | H | S | —NH-c-Pr | 1 | 1 | $C_4H_4O_4 \cdot 0.5\ C_3H_6O$ | 138–145 | 59.23 | 6.77 | 8.82 | 59.47 | 6.90 | 8.37 |
| MeO— | 6-F | O | —NH—Et | 1 | 1 | $C_4H_4O_4$ | 171–172 | 63.53 | 7.53 | 13.07 | 63.29 | 7.69 | 12.75 |
| MeO— | 6-F | O | —NH—Me | 1 | 1 | $C_4H_4O_4$ | 187–188 | 56.73 | 6.19 | 9.92 | 56.48 | 6.39 | 9.67 |
| MeO— | H | O | —NH—Et | 2 | 1 | $0.15\ CH_2Cl_2$ | 141–143 | 67.68 | 8.63 | 12.63 | 67.34 | 8.28 | 12.91 |
| MeO— | H | O | —NH—Me | 2 | 1 | — | 176–178 | 67.30 | 8.30 | 13.85 | 66.91 | 8.17 | 13.52 |

Preferred Procedure for Preparation of Compounds of Formula I

Example 15

1-Cyclopropylcarbonyl-4-(6-methoxy-indan-1-yl)piperazine

An intimate mixture of 6-methoxy-1-indanone (1.6 g, 10 mmol), 1-cyclopropanecarbonylpiperazine (1.5 g, 10 mmol) and titanium(IV) isopropoxide (4 mL, 12 mmol) was heated on the steam bath for 10 minutes. Additional titanium isopropoxide (1 mL, 3 mmol) was added and the mixture stirred for 20 hr. The material was dissolved in ethanol and sodium borohydride added (0.9 g, 22 mmol). After stirring for 1 hr the solution was heated to reflux and more sodium borohydride (0.9 g, 22 mmol) added. When solution had occurred 15% NaOH solution (50 mL) was added. The insoluble material was removed and discarded. The solution was concentrated in vacuo and the residue mixed with ether. The mixture was washed with water and 1N HCl solution. The acid washes were made basic and the mixture was extracted with ether to give the product as an oil which was converted to the fumarate salt and crystallized from acetone to give the salt (1.8 g).

Example 16

1-(2-Methylpropionyl)-4-(6-methoxy-indan-1-yl)piperazine

The title compound was prepared by the above procedure using 6-methoxy-1-indanone (3.2 g, 20 mmol), 1-(2-methylpropionyl)piperazine (3.0 g, 20 mmol), titanium(IV) isopropoxide (8 mL, 24 mmol) and sodium borohydride (2.7 g, 67 mmol) to give 2.2 g of product as the fumarate salt.

Example 17

1-(2-Thienylcarbonyl)-4-(6-methoxy-indan-1-yl)piperazine

The title compound was prepared by the above procedure using 6-methoxy-1-indanone (2.6 g, 13.2 mmol), 1-(2-thienylcarbonyl)piperazine (2.1 g, 13.2 mol), titanium(IV) isopropoxide (5 mL, 15 mmol) and sodium borohydride (2.7 g, 67 mmol) to give 1.5 g of product as the fumarate salt.

Example 18

N-Ethyl-4-(6-methoxy-indan-1-yl)-1-piperazinecarboxamide

The title compound was prepared by the above procedure using 6-methoxy-1-indanone (2.4 g, 15 mmol), N-ethyl-1-piperazinecarboxamide (2.4 g, 15 mol), titanium(IV) isopropoxide (6 mL, 18 mmol) and sodium borohydride (2.7 g, 67 mmol) to give 2.8 g of product as the fumarate salt.

General Procedure for Preparation of Chiral Amides and Ureas

Example 19

The appropriate chiral salt was converted to the free base as described above for preparation of fumarate salts. The $CH_2Cl_2$ solution was then reacted either with the appropriate isocyanate or acid chloride and potassium carbonate as described in the previous general procedures.

Table 3 lists chiral derivatives prepared by these methods.

TABLE 3

Chiral Amides and Ureas

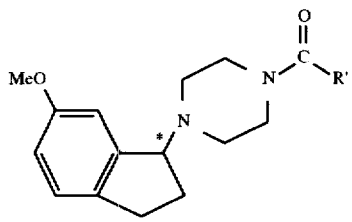

| R' | +/− Salt | mp, °C. | % Calculated | | | % Found | | |
|---|---|---|---|---|---|---|---|---|
| | | | C | H | N | C | H | N |
| -c-Pr | (−) C₄H₄O₄ | 183–184 | 63.45 | 6.78 | 6.73 | 63.11 | 6.71 | 6.62 |
| −NH−Et | (−) C₄H₄O₄ | 145–146 | 60.13 | 6.97 | 10.02 | 59.72 | 6.84 | 9.92 |
| -i-Pr | (−) 1.15 C₄H₄O₄ | 165–165.5 | 62.27 | 7.08 | 6.43 | 62.15 | 6.79 | 6.39 |
| -2-Thienyl | (−) C₄H₄O₄·0.2 H₂O | 210–211 | 59.78 | 5.76 | 6.06 | 59.64 | 6.44 | 6.04 |

Example 20

1-[(2-Furanyl)carbonyl]-4-(6-methoxy-indan-1-yl)piperazine

A solution of (−)-(6-methoxy-indan-1-yl)piperazine (28 mg, 0.12 mmol), 3-furoic acid (58 mg, 0.52 mmol), and 1-hydroxybenzotriazole (17 mg, 0.126 mmole), and 1,3-diisopropylcarbodiimide (16 mg, 0.126 mmol) in CH₂Cl₂ (2 ml) and DMF (2 ml), was shaken for for 5 min and allowed to stand for 18 hr. The reaction mixture was filtered through an SCX Bondesil® (Varian # 1221–3039, 1 g) column. The column was washed with methanol (20 ml) and 0.1N NH₄OH in methanol (2 ml). The product was then eluted from the column using 1N NH₄OH in methanol (5 ml). This last fraction was concentrated in vacuo to give the product (36.8 mg, 94%, ES-MS: 327 (MH⁺).

Table 4 lists other compounds of Formula I prepared by the above method from (−)-(6-methoxy-indan-1-yl)piperazine.

TABLE 4

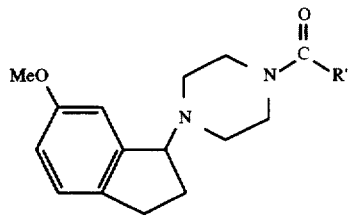

| R' | % yield | MS MH+ |
|---|---|---|
| 2-Furanyl | 96 | 327 |
| 3-Methyl-2-furanyl | 95 | 341 |
| 2-Pyrrolyl | 97 | 326 |
| 1-Methyl-2-pyrrolyl | 91 | 340 |
| 3-Indolyl | 76 | 376 |
| 3-Methyl-2-thienyl | 95 | 357 |
| 3-Thienyl | 96 | 343 |
| 3-Chloro-2-thienyl | 94 | 377, 379 |
| 4,5-Dibromo-2-thienyl | 86 | 499, 501, 503 |
| 1,2,3-Thiadiazol-4-yl | 94 | 345 |
| 2-Chlorophenyl | 94 | 371, 373 |

TABLE 4-continued

| R' | % yield | MS MH+ |
|---|---|---|
| 1-methyl-cyclohexan-1-yl | 84 | 357 |
| −CH=CMe₂ | 98 | 315 |
| −CH₂−Cl | 92 | 309, 311 |
| 5-Bromo-2-furanyl | 84 | 405, 407 |
| 5-Chloro-2-thienyl | 86 | 377, 379 |
| 3-Bromo-2-thienyl | 91 | 421, 423 |
| (+−) −CH(CH₃)−CH₂−CH₃ | 95 | 317 |
| −(CH₂)₈−CH=CH₂ | 94 | 399 |
| −C(CH₃)₂−CH₂−CH₃ | 87 | 331 |
| −CO−Et | 94 | 317 |
| −CH₂−SCH₃ | 94 | 321 |
| 2-Hydroxyphenyl | 100 | 353 |
| −CH₂CH₂−CH=CH₂ | 93 | 315 |

Example 21

Measurement of Binding to Melatonergic Receptors

The melatonergic binding affinities of various compounds of Formula I were determined by the method of Reppert, S. M., Weaver, D. R., and Ebisawa, R. (*Neuron*, Volume 13, 1177–1185, 1994). The assays were incubated at 37° C. for 1 hour, and the reaction was terminated by filtration. The filters were washed with wash buffer. Compounds with IC₅₀ affinity values at or below 250 nM are termed active. The reagents, membrane and other techniques used in the melatonergic binding assays are more fully described below:

1. Reagents (a) 50 mM Tris buffer containing 12.5 mM MgCl₂, and 2mM EDTA, pH 7.4 at 37° C.

(b) Wash buffer: 20 mM Tris base containing 2 mM MgCl₂, pH 7.4 at room temperature.

(c) Melatonin ($10^{-5}$M final concentration).

(d) 2-[$^{125}$I]-Iodomelatonin. 200 pM final concentration
Source: NEN

2. Membrane preparation

NIH 3T3 cells stably transfected with the human $ML_{1B}$ receptor were obtained from S. M. Reppert and maintained. Cells were pelleted when confluent. The supernatant was discarded and the pellets frozen. For preparing membrane homogenates, the pellets are thawed on ice and resuspended in TME buffer, Tris base, $MgCl_2$, EDTA (pH 7.4 at 37° C.), supplemented with aprotinin, leupeptin, and phenylmethylsulfonylfluoride. The cells were then homogenized and centrifuged. The resulting pellet was resuspended with a Dounce homogenizer in TME and frozen. At assay, a small aliquot was thawed on ice and resuspended in TME buffer.

Some compounds of Formula I having $IC_{50}$ values for melatonin binding of 250 nM or less are listed in Table 5. These compounds are considered active. The known melatonin antagonist, luzindole, is listed in Table 5 for comparison.

TABLE 5

Melatonergic Binding of Selected Compounds

| Compound | Melatonin Binding |
| --- | --- |
| 1-(Cyclopropylcarbonyl)-4-(6-methoxy-indan-1-yl)piperazine | *** |
| 1-Butanoyl-4-(6-methoxy-indan-1-yl)piperazine | *** |
| 1-(Cyclobutylcarbonyl)-4-(6-methoxy-indan-1-yl)piperazine | *** |
| 4-(6-Methoxy-indan-1-yl)-1-(2-methyl-propanoyl)piperazine | *** |
| 1-[(1-Methyl-ethenyl)carbonyl]-4-(6-methoxy-indan-1-yl)piperazine | *** |
| (−)-1-(Cyclopropylcarbonyl)-4-(6-methoxy-indan-1-yl)piperazine | *** |
| (−)-4-(6-Methoxy-indan-1-yl)-1-(2-methyl-propanoyl)piperazine | *** |
| (−)4-(6-Methoxy-indan-1-yl)-1-(2-methylthioacetyl)piperazine | *** |
| 1-(Cyclopropylcarbonyl)-4-(6-ethoxy-indan-1-yl)piperazine | *** |
| 4-(6-Methoxy-indan-1-yl)-1-propanoylpiperazine | ** |
| 1-(Cyclopentylcarbonyl)-4-(6-methoxy-indan-1-yl)piperazine | ** |
| 1-(Ethenylcarbonyl)-4-(6-methoxy-indan-1-yl)piperazine | ** |
| 4-(6-Methoxy-indan-1-yl)-1-(2-methyl-propanoyl)homopiperazine | ** |
| 1-(Cyclopropylcarbonyl)-4-(6-methoxy-indan-1-yl)homopiperazine | ** |
| 1-(2,2-dimethyl-propanoyl)-4-(6-methoxy-indan-1-yl)piperazine | ** |
| 1-(Methoxyacetyl)-4-(6-methoxy-indan-1-yl)piperazine | ** |
| (−)-1-[(2,2-Dimethyl-ethenyl)carbonyl]-4-(6-methoxy-indan-1-yl)piperazine | ** |
| (−)-1-(Chloroacetyl)-4-(6-methoxy-indan-1-yl)piperazine | ** |
| 4-(6-Methoxy-indan-1-yl)-1-(2-methyl-butanoyl)piperazine | ** |
| (−)-1-(2,2-Dimethyl-butanoyl)-4-(6-methoxy-indan-1-yl)piperazine | ** |
| (−)-4-(6-Methoxy-indan-1-yl)-1-(2-oxo-butanoyl)piperazine | ** |
| 1-(Cyclopropylcarbonyl)-4-[6-(1-propyloxy)indan-1-yl]piperazine | ** |
| 1-(Cyclopropylcarbonyl)-4-(5-fluoro-6-methoxy-indan-1-yl)piperazine | ** |
| 4-(5-Fluoro-6-methoxy-indan-1-yl)-1-(2-methylpropanoyl)piperazine | ** |
| 1-Acetyl-4-(6-methoxy-indan-1-yl)piperazine | * |
| 4-(6-Methoxy-indan-1-yl)-1-(2-methyl-propanoyl)piperazine | * |
| 1-(Cyclopropylcarbonyl)-4-(indan-1-yl)piperazine | * |
| (−)-1-[(1-Methylcyclohexyl)carbonyl]-4-(6-methoxy-indan-1-yl)piperazine | * |
| (−)-4-(6-Methoxy-indan-1-yl)-1-(10-undecenoyl)piperazine | * |
| (−)-4-(6-Methoxy-indan-1-yl)-1-(4-pentenoyl)piperazine | * |
| 1-(Cyclopropylcarbonyl)-4-(6-nonyloxy-indan-1-yl)piperazine | * |
| 1-(Cyclopropylcarbonyl)-4-(6-ethyl-indan-1-yl)piperazine | * |
| 4-(6-Ethyl-indan-1-yl)-1-(2-methylpropanoyl)piperazine | * |
| 4-(6-Methoxy-indan-1-yl)-1-[(2-thienyl)carbonyl]piperazine | *** |
| 1-[(2-Furanyl)carbonyl]-4-(6-methoxy-indan-1-yl)piperazine | *** |
| (−)-4-(6-Methoxy-indan-1-yl)-1-[(2-thienyl)carbonyl]piperazine | *** |
| (−)-1-[(2-Furanyl)carbonyl]-4-(6-methoxy-indan-1-yl)piperazine | *** |
| (−)-4-(6-Methoxy-indan-1-yl)-1-[(3-methyl-furan-2-yl)carbonyl]piperazine | *** |
| (−)-4-(6-Methoxy-indan-1-yl)-1-[(1-methyl-pyrrol-2-yl)carbonyl]piperazine | *** |
| (−)-4-(6-Methoxy-indan-1-yl)-1-[(1-methyl-thien-2-yl)carbonyl]piperazine | *** |
| (−)-4-(6-Methoxy-indan-1-yl)-1-[(3-thienyl)carbonyl]piperazine | *** |
| (−)-1-[(3-Chlorohien-2-yl)carbonyl]-4-(6-methoxy-indan-1-yl)-1-piperazine | *** |
| (−)1-[(3-Bromothien-2-yl)carbonyl]-4-(6-Methoxy-indan-1-yl)piperazine | *** |
| (−)-1-(2-Hydroxybenzoyl)-4-(6-methoxy-indan-1-yl)piperazine | *** |
| (−)-1-[(3-Furanyl)carbonyl]-4-(6-methoxy-indan-1-yl)piperazine | ** |
| (−)-4-(6-Methoxy-indan-1-yl)-1-[(1H-pyrrol-2-yl)carbonyl]-piperazine | ** |
| (−)-4-(6-Methoxy-indan-1-yl)-1-[(1,2,3-thiadiazol-4-yl)carbonyl]-piperazine | ** |
| (−)-1-[(5-Bromo-furan-2-yl)carbonyl]-4-(6-methoxy-indan-1-yl)piperazine | ** |
| (−)-1-(Benzoyl)-4-(6-methoxy-indan-1-yl)piperazine | * |
| (−)-1-[(1H-indol-3-yl)carbonyl]-4-(6-methoxy-indan-1-yl)piperazine | * |
| (−)-1-[(4,5-Dibromo-thien-2-yl)carbonyl]-4-(6-methoxy-indan-1-yl)piperazine | * |
| (−)-1-(2-Chlorobenzoyl)-4-(6-methoxy-indan-1-yl)pipetazine | * |
| (−)-1-[(5-Chloro-thien-2-yl)carbonyl]-4-(6-methoxy-indan-1-yl)piperazine | * |
| 1-(Ethoxycarbonyl)-4-(6-methoxy-indan-1-yl)piperazine | * |
| N-Cyclopropyl-4-(6-methoxy-indan-1-yl)piperazine-1-carboxamide | *** |
| N-Methyl-4-(6-methoxy-indan-1-yl)piperazine-1-carboxamide | *** |
| (−)-N-Ethyl-4-(6-methoxy-indan-1-yl)piperazine-1-carboxamide | *** |
| N-Cyclopropyl-4-(6-methoxy-indan-1-yl)piperazine-1-carboxamide | *** |
| N-(n-Propyl)-4-(6-methoxy-indan-1-yl)piperazine-1-carboxamide | ** |
| N-Ethyl-4-(6-methoxy-indan-1-yl)piperazine-1-carboxamide | ** |
| N-Ethyl-4-(6-methoxy-indan-1-yl)homopiperazine-1-carboxamide | ** |
| N-(1-Methylethyl)-4-(6-methoxy-indan-1-yl)piperazine-1-carboxamide | ** |
| N,N-Dimethyl-4-(6-methoxy-indan-1-yl)piperazine-1-carboxamide | ** |
| N-Ethyl-4-(6-ethoxy-indan-1-yl)piperazine-1-carboxamide | ** |
| N-Ethyl-4-(6-propyloxy-indan-1-yl)piperazine-1-carboxamide | ** |
| N-Ethyl-4-(6-nonyloxy-indan-1-yl)piperazine-1-carboxamide | ** |
| N-Ethyl-4-(5-fluoro-6-methoxy-indan-1-yl)piperazine-1-carboxamide | ** |
| N-Methyl-4-(5-fluoro-6-methoxy-indan-1-yl)piperazine- | ** |

TABLE 5-continued

Melatonergic Binding of Selected Compounds

| Compound | Melatonin Binding |
|---|---|
| 1-carboxamide | |
| 1-Acetyl-4-(7-methoxy-tetralin-1-yl)piperazine | ** |
| 1-(1-Butanoyl)-4-(7-methoxy-tetralin-1-yl)piperazine | ** |
| 1-(Cyclopropylcarbonyl)-4-(7-methoxy-tetralin-1-yl)piperazine | * |
| N-Methyl-4-(7-methoxy-tetralin-1-yl)piperazine-1-carboxamide | ** |
| N-Ethyl-4-(7-methoxy-tetralin-1-yl)piperazine-1-carboxamide | * |
| Luzindole | * |

***: $IC_{50} < 10$ nM;
**: $10 < IC_{50} < 100$ nM;
*: $100 < IC_{50} < 250$ nM.

Reasonable variations, such as those which would occur to a skilled artisan, can be made herein without departing from the scope of the invention.

We claim:

1. A compound of Formula I:

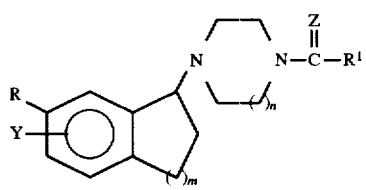

wherein:

R is H, $C_{1-4}$ alkyl, or $C_{1-9}$ alkoxy;

m is 1;

n is 1 or 2;

Y is H, $C_{1-4}$ alkoxy, or halogen;

Z is O or S; and $R^1$ is $C_{1-6}$ alkyl (straight or branched), $C_{1-6}$ haloalkyl, $C_{1-4}$ thioalkoxy substituted $C_{1-4}$ alkyl, $C_{1-6}$ alkoxy substituted $C_{1-4}$ alkyl, $C_{2-20}$ alkenyl (straight or branched), $C_{3-6}$ cycloalkyl, phenyl, thienyl, pyrrolyl, furanyl, thiadiazolyl, indolyl, substituted phenyl, thienyl, pyrrolyl or furanyl wherein the substituent is selected from group consisting of hydroxy, chloro, bromo and methyl or $NR^2R^3$ wherein $R^2$ and $R^3$ are independently hydrogen, $C_{1-3}$ alkyl or $C_{3-6}$ cycloalkyl.

2. The compound of claim 1 wherein R is methoxy, m is 1, n is 1 and Z is O.

3. The compound of claim 2 wherein $R^1$ is $C_{3-5}$ cycloalkyl, thienyl, furanyl, pyrrolyl, phenyl substituted phenyl, thienyl, pyrrolyl or furanyl wherein the substituent is selected from group consisting of hydroxy, chloro, bromo and methyl or thioalkoxyalkyl.

4. The compound of claim 3 selected from the group consisting of:

(−)-4-(6-Methoxy-indan-1-yl)-1-(2-methylthioacetyl)piperazine (−)-4-(6-Methoxy-indan-1-yl)-1-|(2-thienyl)carbonyl| piperazine;

1-(Cyclopropylcarbonyl)-4-(6-methoxy-indan-1-yl)piperazine;

(−)-1-(Cyclopropylcarbonyl)-4-(6-methoxy-indan-1-yl)piperazine;

1-(Cyclopentylcarbonyl)-4-(6-methoxy-indan-1-yl)piperazine;

1-|(2-Furanyl)carbonyl|-4-(6-methoxy-indan-1-yl)piperazine;

4-(6-Methoxy-indan-1-yl)-1-|(2-thienyl)carbonyl| piperazine (−)-1-|(3-Chlorothien-2-yl)carbonyl|-4-(6-methoxy-indan-1-yl)-1-piperazine;

(−)-4-(6-Methoxy-indan-1-yl)-1-|(1-methyl-pyrrol-2-yl)carbonyl|piperazine;

(−)-1-|(2-Furanyl)carbonyl|-4-(6-methoxy-indan-1-yl)piperazine;

(−)-4-(6-Methoxy-indan-1-yl)-1-|(3-methyl-furan-2-yl)carbonyl|piperazine;

(−)-1-(2-Hydroxybenzoyl)-4-(6-methoxy-indan-1-yl)piperazine;

(−)1-|(3-Bromothien-2-yl)carbonyl|-4-(6-Methoxy-indan-1-yl)piperazine;

(−)-4-(6-Methoxy-indan-1-yl)-1-|(3-methyl-thien-2-yl)carbonyl|piperazine;

(−)-4-(6-Methoxy-indan-1-yl)-1-|(3-thienyl)carbonyl| piperazine; and 1-(Cyclobutylcarbonyl)-4-(6-methoxy-indan-1-yl)piperazine.

5. The compound of claim 2 wherein $R^1$ is $NR^2R^3$.

6. The compound of claim 5 selected from the group consisting of:

(−)-N-Ethyl-4-(6-methoxy-indan-1-yl)piperazine-1-carboxamide;

N-Methyl-4-(6-methoxy-indan-1-yl)piperazine-1-carboxamide;

N-(n-Propyl)-4-(6-methoxy-indan-1-yl)piperazine-1-carboxamide;

N-Ethyl-4-(6-methoxy-indan-1-yl)piperazine-1-carboxamide;

N-(1-Methylethyl)-4-(6-methoxy-indan-1-yl)piperazine-1-carboxamide;

N-Cyclopropyl-4-(6-methoxy-indan-1-yl)piperazine-1-carboxamide; and

N-Cyclopropyl-4-(6-methoxy-indan-1-yl)piperazine-1-carboxamide.

7. The compound of claim 2 wherein $R^1$ is $C_{2-4}$ alkenyl.

8. The compound of claim 7 selected from the group consisting of:

1-(Ethenylcarbonyl)-4-(6-methoxy-indan-1-yl)piperazine; and

1-|(1-Methyl-ethenyl)carbonyl|-4-(6-methoxy-indan-1-yl)piperazine.

9. The compound of claim 2 wherein $R^1$ is $C_{1-6}$ alkyl.

10. The compound of claim 9 selected from the group consisting of:

4-(6-Methoxy-indan-1-yl)-1-(2-methyl-propanoyl)piperazine;

1-Butanoyl-4-(6-methoxy-indan-1-yl)piperazine;

1-(2,2-dimethyl-propanoyl)-4-(6-methoxy-indan-1-yl)piperazine; and (−)-4-(6-Methoxy-indan-1-yl)-1-(2-methyl-propanoyl)piperazine.

11. The compound of claim 1, (−)-N-Ethyl-4-(6-methoxy-indan-1-yl)piperazine-1-carboxamide.

12. The compound of claim 1, (−)-1-(Cyclopropylcarbonyl)-4-(6-methoxy-indan-1-yl)piperazine.

13. The compound of claim 1, (−)-4-(6-Methoxy-indan-1-yl)-1-|(2-thienyl)carbonyl|piperazine.

14. The compound of claim 1, 1-(Cyclopropylcarbonyl)-4-(6-methoxy-indan-1-yl)piperazine.

15. The compound of claim 1, 4-(6-Methoxy-indan-1-yl)-1-(2-methyl-propanoyl)piperazine.

16. The compound of claim 1, 1-(Cyclopropylcarbonyl)-4-(6-ethoxy-indan-1-yl)piperazine.

17. The compound of claim 1 selected from the group consisting of:

1-(Cyclopropylcarbonyl)-4-(6-methoxy-indan-1-yl)homopiperazine;

N-Ethyl-4-(6-methoxy-indan-1-yl)homopiperazine-1-carboxamide; and 4-(6-Methoxy-indan-1-yl)-1-(2-methyl-propanoyl)homopiperazine.

18. A pharmaceutical composition for treating a sleep or circadian rhythm disorder in a patient in need of such treatment comprising an effective amount of a compound of claim 1 and a suitable amount of a pharmaceutically acceptable carrier.

19. A method of treating a sleep disorder in a patient in need of such treatment comprising the administration to said patient of an effective amount of a compound of claim 1.

20. A pharmaceutical composition for treating depression in a patient in need of such treatment comprising an effective amount of a compound of claim 1 and a suitable amount of a pharmaceutically acceptable carrier.

21. A method of treating depression in a patient in need of such treatment comprising the administration to said patient of an effective amount of a compound of claim 1.

* * * * *